US00PP19434P3

(12) United States Plant Patent
Vorsa

(10) Patent No.: US PP19,434 P3
(45) Date of Patent: Nov. 11, 2008

(54) CRANBERRY PLANT NAMED 'CNJ97-105-4'

(50) Latin Name: *Vaccinium macrocarpon Ait*
Varietal Denomination: CNJ97-105-4

(75) Inventor: Nicholi Vorsa, Atco, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 119 days.

(21) Appl. No.: 11/483,065

(22) Filed: Jul. 7, 2006

(65) Prior Publication Data

US 2008/0010710 P1 Jan. 10, 2008

(51) Int. Cl.
*A01H 5/00* (2006.01)

(52) U.S. Cl. ..... Plt./156

(58) Field of Classification Search ..... Plt./156
See application file for complete search history.

*Primary Examiner*—Kent L Bell
(74) *Attorney, Agent, or Firm*—Klarquist Sparkman, LLP

(57) ABSTRACT

A new cranberry variety distinguished by significantly higher yields, higher anthocyanin content (red pigment), higher stolon vigor, and earlier flowering phenology.

2 Drawing Sheets

STATEMENT REGARDING FEDERALLY SPONSORED RESEARCH OR DEVELOPMENT

This invention was made in part with United States Government support awarded by the U.S. Department of Agriculture, Cooperative State Research, Education and Extension Service, under grant SRG 88-34155-3491. Therefore, the Government may have certain rights in this invention.

Latin name of the genus and species of the plant claimed: *Vaccinium macrocarpon Ait.*

Variety denomination: 'CNJ97-105-4'.

BACKGROUND OF THE INVENTION

The present invention relates to a new American cranberry variety of distinctive lineage having significantly higher yields and stolon vigor, higher anthocyanin content (red pigment), and earlier flowering phenology, as compared to currently cultivated commercial varieties known to the inventor. The new variety, 'CNJ97-105-4', was derived from a cross between 'LeMunyon' (unpatented) and '#35' (unpatented), two varieties which are genetically distinct from the majority of cranberries in production today. As such, 'CNJ97-105-4' offers growers an opportunity to increase the genetic diversity of their cranberry beds while increasing yields. 'CNJ97-105-4' was originally selected from over 1,700 seedlings growing in cultivated test plots in Chatsworth, N.J.

The American cranberry (*Vaccinium macrocarpon Ait.*) is a temperate, woody perennial plant species native to North America. The United States is the largest cranberry producer, with Wisconsin and Massachusetts representing the majority of acreage and production, followed by New Jersey, Oregon and Washington. The cranberry industry relies on relatively few cranberry varieties, representing a narrow genetic base. These varieties are clonally-propagated and include selections from native populations and first generation hybrids. Varieties selected from native cranberry populations, from as far back as 1850, are still being cultivated. The cultivars 'Ben Lear' (unpatented) and 'Early Black' (unpatented) are grown in significant acreage. First generation hybrid varieties were developed from one cycle of breeding and selection that was conducted by the United States Department of Agriculture, in cooperation with state Agricultural Experiment Stations in the 1940's. The USDA breeding program released a series of unpatented varieties in the 1950's including the most widely grown cultivar 'Stevens' (unpatented), which was originally selected from test plots in Pemberton, N.J. The variety '#35' (unpatented) (a parent of CNJ97-105-4) also originated from this USDA breeding program and was acquired by some commercial entities. Recognized for its yield potential, '#35' (unpatented) was not widely accepted due to relatively poor fruit color development.

Varieties having high anthocyanin production along with consistently high productivity have become essential for commercial success in cranberry production. In addition, varieties having higher resistance to fruit rot are more suitable for fruit rot prone growing areas. Fruit crop productivity is a function of inherent differences among varieties for traits such as stolon vigor, upright density, inflorescence bud production, fruit set and fruit size. Varieties with high stolon vigor will establish more rapidly and reduce the number of years required to achieve maximal production. However, after bed establishment, varieties must transition to optimal sexual reproduction mode, and optimal upright density, to achieve high crop production. Cranberry inflorescence bud primordia are set on uprights during the completion of the fruit development period and overwinter in a dormant state, before resuming growth the subsequent spring. Thus, the crop load of a given year, may impact the subsequent year's crop, contributing to the pronounced biennial bearing habit common to many varieties. Productivity is also subject to environmental effects, e.g., heat and light intensity stresses, cold (frost) stress, water stress (drought and excess), disease, insects and certain pesticides.

TAcy (total anthocyanin content) is currently a fruit quality component of processed cranberries, having a minimum acceptable value, as well as premiums for fruit with higher TAcy values. Cranberries from a given bed are measured for TAcy content. TAcy is measured in terms of mg of anthocyanin per 100 g fruit using a standard spectrophotometric (520 nm) method. Earlier ripening varieties, which typically have higher TAcy, allow for earlier harvesting of a crop. Anthocyanin synthesis occurs predominately in the fruit epidermis, resulting in a generally negative correlation between fruit size and TAcy. The Rutgers University cranberry breeding program quantitatively measured TAcy along with mean fruit size, and selected only those progeny that were above the regression line representing the mean relationship between fruit size and TAcy.

New Jersey uniquely offers an ideal environment for cranberry breeding because of the climate, soils and water. Of all the cranberry production areas in North America, New Jersey conditions subject the cranberry to the highest disease pressure and heat stress. The plant must tolerate high heat stress and vegetative diseases during the growing season. Over 15 pathogens are known to incite cranberry fruit rot in New Jersey, and the fruit is also subject to heat scald and physiological breakdown. Thus, selection under New Jersey conditions offers the best opportunity to identify varieties with higher resistance to disease, scald, and heat stress.

The Rutgers University cranberry breeding program, in Chatsworth, N.J., was initiated in 1985 to take advantage of this unique selection pressure. The program's methods were designed to duplicate, as much as possible, the environment of a commercial bed. Thus, breeding plots of 1.5 m×1.5 m were established with multiple plants and allowed to fill in to form a dense canopy. Two to four years after planting, yield of a given plot was evaluated over a four year minimum to provide for biennial bearing assessment. Selection of parental material is critical; parental clones were selected based on their field phenotypic performance and crossed in various combinations in order to enhance traits and/or combine the most desirable traits from both parents into one genotype, i.e., variety. Traits being evaluated in Rutgers University's cranberry breeding program include yield, fruit rot susceptibility/resistance, scald, stolon and upright vigor, total anthocyanin content (TAcy), soluble solids (Brix), and tiltratable acidity.

The new variety, 'CNJ97-105-4', resulted from crossing the variety 'LeMunyon' (unpatented) as the seed parent, with the variety '#35' (unpatented) as the pollen parent. The plant was originally selected from a group of plants sexually derived from the same parents as the new variety and that were grown in a field trial of over 1,700 seedlings derived from 57 cross combinations. The 1.5 m×1.5 m plots were planted in 1999 in Chatsworth, N.J. Results from this trial showed that 'CNJ97-105-4' performed significantly better than standard varieties. In 2003, 'CNJ97-105-4', along with 76 other selections, was planted in a replicated trial with 3 m×3 m plots in Chatsworth, N.J. for additional evaluation. 'CNJ97-105-4' was also planted in larger evaluation beds in 2004, in Browns Mills, N.J. (0.5 acres) and City Point, Wis. (1.0 acres) for evaluation in a larger scale environment.

'CNJ97-105-4' is a new cranberry variety selected under New Jersey's stressful conditions, which offers a unique germplasm background and the potential for rapid bed establishment and exceptionally high yields.

BRIEF SUMMARY OF THE INVENTION

The 'CNJ97-105-4' variety is distinguished from other cranberry varieties due to the following unique combination of characteristics: significantly higher yield, higher total anthocyanins, earlier flowering phenology, and greater vigor than 'Ben Lear' (unpatented) and 'Stevens' (unpatented) varieties.

'CNJ97-105-4' has been asexually reproduced by cuttings at the Marucci Center for Blueberry & Cranberry Research & Extension Center, Chatsworth, N.J. since 1999. Over that period, no evidence of off-types of 'CNJ97-105-4' has been observed or reported. Thus, it is concluded that 'CNJ97-105-4' is stable and reproduces true to type in successive generations of asexual reproduction.

The following detailed description concerns the variety 'CNJ97-105-4'. The original plant and vegetative propagules have been observed growing in cultivated areas in Chatsworth and Browns Mills, N.J., and City Point, Wis. Certain characteristics of this variety, such as growth and color, may change with changing environmental conditions (such as light, temperature, moisture, nutrient availability, or other factors). Color descriptions and other terminology are used in accordance with their ordinary dictionary descriptions, unless the context clearly indicates otherwise. Color designations are made with reference to the Royal Horticultural Society (RHS) Color Chart.

Figure 1:
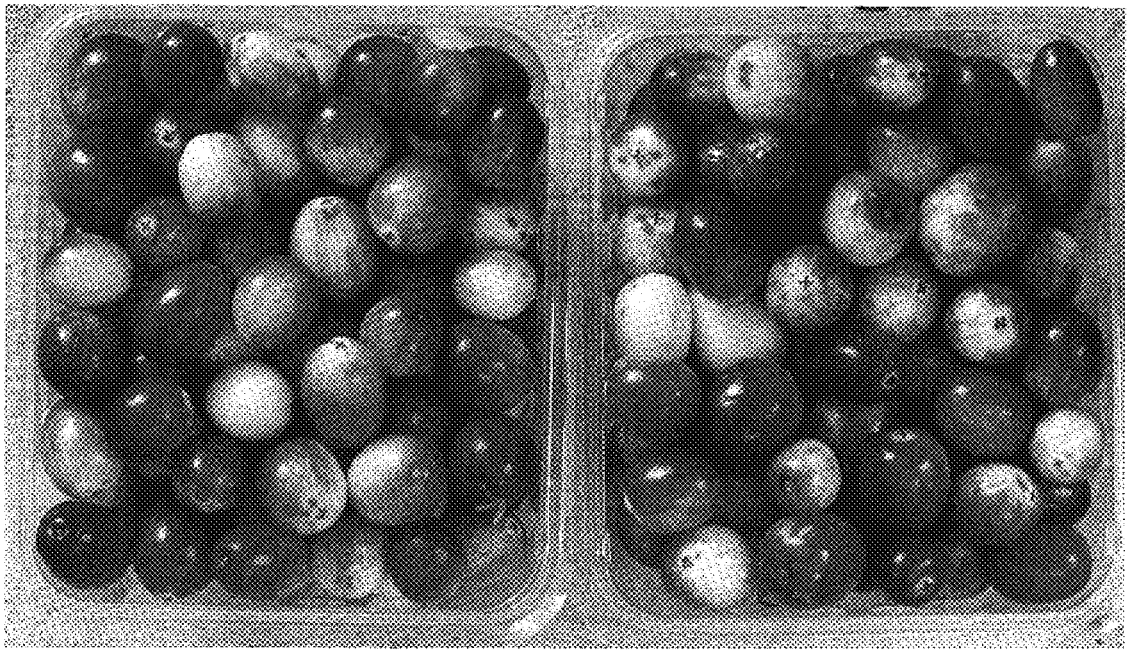
FIG. 1 compares 'Stevens' (unpatented) fruit (on the left) with 'CNJ97-105-4' fruit (on the right), harvested on Oct. 19, 2005 from the same cranberry bed in Chatsworth, N.J.

The colors of an illustration of this type may vary with lighting and other conditions under which conditions and, therefore, color characteristics of this new variety should be determined with reference to the observations described herein, rather than from these illustrations alone.

DETAILED BOTANICAL DESCRIPTION

The following detailed description of the 'CNJ97-105-4' variety is based on observations of plants growing in the field in Chatsworth, N.J. The characteristics of the variety were compared to 'Stevens' (unpatented) and 'Ben Lear' (unpatented), two of the most widely used cranberry varieties. The observed plantings were 1–6 years of age. Comparison to parents: 'CNJ97-105-4' can be distinguished from its parents by its larger fruit size, higher yield and more vigorous plant growth. In addition, 'CNJ97-105-4 has darker fruit' (higher total anthocyanins) than its pollen parent, #35.

Scientific name: *Vaccinium macrocarpon Ait.*

Parentage:

*Seed parent.*—The variety 'LeMunyon' (selected in 1960 from native New Jersey vines by Normal LeMunyon, Indian Mills, N.J.) (unpatented).

*Pollen parent.*—The variety '#35' (derived from a 'Howes'×'Searles' cross) (unpatented).

Plant:

*Vigor.*—In a replicated trial planted Jun. 16, 2003 and consisting of 80 advanced selections and standard varieties, 'CNJ97-105-4' had 35% cover after one year's growth, as compared to 'Stevens' (unpatented) with 23% cover and 'Ben Lear' (unpatented) with 28% cover (Jun. 21, 2004). General observations of 'CNJ97-105-4' plantings indicate exceptional plant vigor.

*Growth habit.*—Trailing shrub with very slender stems.

*Runner length.*—Average runner length was 39.9 cm in a 2-yr. old field planting, as compared to 'Stevens' (unpatented) at 32.3 cm and 'Ben Lear' (unpatented) at 29.1 cm.

*Length of the Upright* (*vertical shoot arising from a stolon, commonly referred to as an Upright*).—Average length was 9.6 cm, compared to 9.4 cm in 'Stevens' (unpatented).

*Stem diameter.*—1.5 mm at base of current year's growth, the same as 'Stevens' (unpatented).

*Internodes.*—Average internode length was about 8.9 mm on a 1-year old runner, compared to 7.5 mm in 'Stevens' (unpatented).

*Productivity.*—In established test plots in Chatsworth, N.J. 'CNJ97-105-4' produced an average of 474 g of berries/sq. ft. (51 g/dm$^2$) in comparison to 'Stevens' (unpatented) yield of 285 g/sq. (31 g/dm$^2$) (5-year averages, see Table 1).

*Hardiness.*—Hardy in Zones 4–7 (from USDA Misc. Publ. 814).

*Disease resistance.*—No disease resistance data available for foliar or root pathogens. One of 'CNJ97-105-4's parents, '#35' (unpatented), has been noted to have some resistance to Phytophthora root rot.

Leaves: The length, width and other measurements were obtained from observations of 20 typical fully developed leaves on Nov. 16, 2004 from plants of the new variety in a 6-yr. old field plot. Color was determined on actively growing plants.

*Texture.*—Coriaceous (leathery).

*Length.*—Average leaf length was 10.2 mm, with a range of 7.9–11.9 mm.

*Width.*—Average leaf width was 4.2 mm, with a range of 3.6–5.1 mm.

*Shape.*—Elliptic (2.4:1 ratio).

*Apex shape.*—Rounded.

*Base shape.*—Rounded, nearly sessile.

*Margin.*—Entire, slightly revolute.

*Leaf color.*—Upper leaf surface color ranges from bright green (RHS 143C) in new growth to deep green in mature leaves (RHS 139A).

*Lower leaf coloration.*—Greyed-green (RHS 191A).

*Pubescence.*—A small number of non-glandular trichomes found at tip and margins of leaf.

Flowers:

*Size and shape.*—Slender, nodding flowers on erect pedicels and in clusters of 3–9 flowers, corolla long-conic in bud, upon opening the petals are strongly reflexed and divided nearly to the base; typical open flower measuring about 10 mm across.

*Flower depth.*—Because the petals are so strongly reflexed at anthesis, the flowers essentially have no "depth".

*Bud size and shape.*—Conic in shape, 7.3 mm long by 2.9 mm wide.

*Petals.*—4 petals per flower; narrow and revolute in shape, petals are 9.0 mm long and 2.3 mm wide at the base, narrowing to a pointed apex, margins are smooth.

*Calyx.*—The calyx consists of 4 fused sepals, and is 2 mm wide by 2.8 mm long.

*Color.*—Unopened bud: deep pink (RHS 68C). Opened flower: pale pink (RHS 69A & 69B).

*Petals.*—4 petals per flower; narrow and revolute in shape.

*Flowering phenology.*—Bloom typically begins in late May and continues until late June depending on the season. 'CNJ97-105-4' has an earlier flowering phenology, achieving 50% anthesis (bloom) on Jun. 19, 2003, Jun. 7, 2004, and Jun. 15, 2005, 3–5 days before 'Stevens' (unpatented) each year.

*Mean number of flowers per upright.*—5.4 flowers, compared to 4.9 in 'Stevens' (unpatented).

*Mean number of flowers per ft$^2$.*—In 2004, 'CNJ97-105-4' had an average of 706 flowers per ft$^2$, compared to 'Stevens' (unpatented) with 619 flowers per ft$^2$.

Fruit: Observations are from 30 typical fruit harvested from test plots in Chatsworth, N.J. on Oct. 10, 2004 (FIG. 1).

*Shape.*—Widely elliptic, with rounded stem end and rounded calyx end.

*Size.*—2.2 cm long and 1.7 cm wide.

*Skin.*—Shiny, with little to no bloom.

*Flesh color.*—White (RHS155c & 155d).

*Skin color.*—Ranged from RHS 46B (red group) for the lightest berries, RHS 53A (red group) for medium berries, to RHS 187A (greyed-purple group) for the darkest.

*Stem pit.*—Medium in width (1.2 mm) and barely indented (0.3 mm).

*Average weight.*—Fruit collected yearly from 1 ft$^2$ samples in test plots had an average weight of 2.2 g, similar to 'Stevens' (unpatented) at 2.1 g (Table 2, five year mean).

*Number of seeds.*—An average of 18 seeds per fruit, similar to 'Stevens' (unpatented).

*Seed color.*—Greyed-orange (RHS 165b & 166c).

*Fruit per upright.*—3 to 7 per cluster.

*Fruit chemistry.*—100 g samples of fruit were harvested each year from test plots in Chatsworth, N.J. and evaluated for fruit chemistry. 'CNJ97-105-4' had TAcy values averaging 100% greater than 'Stevens' (unpatented) in September and averaging 41% greater in October (Table 3, five year mean). 'CNJ97-105-4' had Brix (% soluble solids) and titratable acidity values that were comparable to 'Stevens' (unpatented): 7.9% vs. 8.1% Brix; and 2.3% vs. 2.4% titratable acidity.

Figure 2:
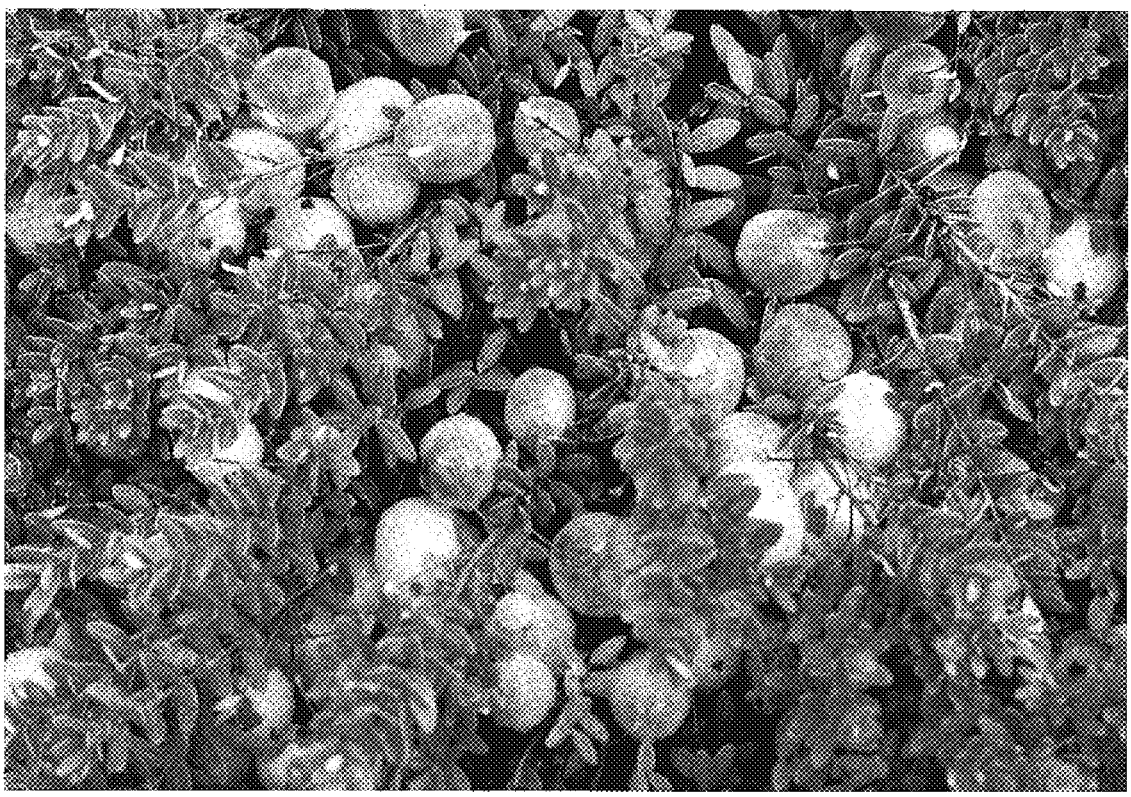
FIG. 2 shows the density of fruit and multiple fruits per upright on 'CNJ97-105-4' plants, on Aug. 15, 2005, Chatsworth, N.J.

*Fruit production.*—First picking date in New Jersey was September 10, and last picking date was October 15. Average production was 474 g of berries/ft$^2$ (51 g/dm$^2$, equivalent to 456 barrels/acre), compared to 'Stevens' (unpatented) yield of 285 g/ft$^2$ (5 yr. mean in NJ test plots, Table 1). Because fruit samples from 'CNJ97-105-4' have almost the same average weight as 'Stevens' (unpatented), the significantly higher yields of 'CNJ97-105-4' are achieved largely from higher fruit density (FIG. 2).

*Usage.*—Processing and fresh fruit.

*Fruit taste.*—Slightly astringent and tart.

*Disease Resistance.*—In New Jersey, in a trial where fungicides were used and disease pressure was severe, 'CNJ97-105-4' had a 5-year average of 6.3% fruit rot (2001–2005), compared to 9.6% fruit rot in 'Stevens' (unpatented).

TABLE 1

Yield of 'CNJ97-105-4', as compared to 'Stevens' (unpatented), in a research trial established May 1999 in Chatsworth, NJ.

| | Total yield, g/ft$^2$ | | | | | 01-05 |
|---|---|---|---|---|---|---|
| Cultivar | 2001 | 2002 | 2003 | 2004 | 2005 | mean |
| 'CNJ97-105-4' | 614 | 352 | 352 | 500 | 606 | 474 |
| 'Stevens' | 210 | 227 | 331 | 343 | 351 | 285 |

TABLE 2

Fruit weight of 'CNJ97-105-4', as compared to 'Stevens' (unpatented), in a research trial established May 1999 in Chatsworth, NJ.

| | Fruit wt., g/berry | | | | | 01-05 |
|---|---|---|---|---|---|---|
| Cultivar | 2001 | 2002 | 2003 | 2004 | 2005 | mean |
| 'CNJ97-105-4' | 2.1 | 2.1 | 2.3 | 2.1 | 2.2 | 2.2 |
| 'Stevens' | 2.2 | 2.2 | 2.3 | 1.9 | 2.0 | 2.1 |

TABLE 3

Fruit color comparisons (total anthocyanins) of 'CNJ97-105-4' and 'Stevens' (unpatented) in a research trial established May 1999 in Chatsworth, NJ.

| | TAcy (mg/100 g fruit) September | | | | | |
|---|---|---|---|---|---|---|
| Cultivar | 2001 | 2002 | 2003 | 2004 | 2005 | mean |
| 'CNJ97-105-4' | 12 | 34 | 13 | 20 | 10 | 18 |
| 'Stevens' | 5 | 16 | 7 | 11 | 6 | 9 |

| | TAcy (mg/100 g fruit) October | | | | | |
|---|---|---|---|---|---|---|
| Cultivar | 2001 | 2002 | 2003 | 2004 | 2005 | mean |
| 'CNJ97-105-4' | 52 | 65 | 24 | 35 | 21 | 41 |
| 'Stevens' | 37 | 44 | 28 | 29 | 11 | 29 |

I claim:

1. A new and distinct variety of cranberry plant, substantially as herein shown and described.

* * * * *

'Stevens' (unpatented) 'CNJ97-105-4'

UNITED STATES PATENT AND TRADEMARK OFFICE

CERTIFICATE OF CORRECTION

PATENT NO. : PP 19,434 P3
APPLICATION NO. : 11/483065
DATED : November 11, 2008
INVENTOR(S) : Nicholi Vorsa It is certified that error appears in the above-identified patent and that said Letters Patent is hereby corrected as shown below:

Column 3, line 41, “tiltratable” should read --titratable--

Column 4, line 55, “Normal” should read --Norman--

Column 5, line 17, “285 g/sq.” should read --285 g/sq. ft.--

Signed and Sealed this

Seventh Day of July, 2009

JOHN DOLL
*Acting Director of the United States Patent and Trademark Office*